(12) United States Patent
Jolidon et al.

(10) Patent No.: US 6,846,832 B2
(45) Date of Patent: Jan. 25, 2005

(54) 2,3-DIHYDRO-ISOINDOL-1-ONE DERIVATIVES

(75) Inventors: Synese Jolidon, Blauen (CH); Rosa Maria Rodriguez-Sarmiento, Basel (CH); Andrew William Thomas, Birsfelden (CH); Rene Wyler, Zurich (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 10/625,116

(22) Filed: Jul. 22, 2003

(65) Prior Publication Data

US 2004/0082603 A1 Apr. 29, 2004

(30) Foreign Application Priority Data

Aug. 7, 2002 (EP) .............................. 02017676

(51) Int. Cl.$^7$ ................. A61K 31/4035; A61K 31/435; C07D 209/44; C07D 221/02
(52) U.S. Cl. ...................... 514/299; 514/416; 546/183; 548/470
(58) Field of Search ........................ 546/183; 548/470; 514/299, 416

(56) References Cited

U.S. PATENT DOCUMENTS

| | | | |
|---|---|---|---|
| 5,100,914 A | | 3/1992 | Rendenbach-Mueller et al. |
| 5,304,556 A | * | 4/1994 | Yamamoto et al. .......... 514/243 |
| 5,326,760 A | * | 7/1994 | McElroy et al. .......... 514/235.2 |
| 6,660,736 B2 | * | 12/2003 | Cesura et al. ............ 514/235.2 |

FOREIGN PATENT DOCUMENTS

| | | |
|---|---|---|
| EP | 0 363 793 | 4/1990 |
| EP | 0 754 455 | 1/1997 |
| WO | WO 96/40095 | 12/1996 |
| WO | WO 97/33572 | 9/1997 |
| WO | WO 01/34172 | 5/2001 |
| WO | WO 03 080573 | 10/2003 |

OTHER PUBLICATIONS

Gnerre Carmela, et al., Journal of Medicinal Chemistry, vol. 43, No. 25, pp. 4747–4758 (2000).
Bach et al., Proc. Natl. Acad. Sci. USA 85:4934–4938 (Jul. 1988).
Cesura & Pletscher, Prog. Drug Research 38:171–297 (1992).
Fowler et al., J. Neural. Transm. 49:1–20 (1980).
M. S. Benedetti et al., Biochem. Pharmacol. 38:555–561 (1989).
Saura et al., Neuroscience 70:755–774 (1996).
Bentué–Ferrer et al., in CNS Drugs 6:217–236 (1996).
Gardner et al., J. Clin. Psychiatry 57(3): 99–104 (1996).
Schlaeger & Christensen, Cytotechnology 30: 71–83 (1999).
Zhou & Panchuk–Voloshina, Analytical Biochemistry 253: 169–174 (1997).
Grethe et al., J. Org. Chem. 33: 494–503 (1968).

* cited by examiner

*Primary Examiner*—Golam M M Shameem
(74) *Attorney, Agent, or Firm*—George W. Johnston; Patricia S. Rocha-Tramaloni; Kimberly J. Prior

(57) ABSTRACT

2,3-Dihydro-isoindol-1-one derivatives, processes for their production, their use as pharmaceuticals and pharmaceutical compositions comprising them, for the prevention and treatment of diseases which are mediated by monoamine oxidase B.

49 Claims, No Drawings

2,3-DIHYDRO-ISOINDOL-1-ONE DERIVATIVES

FIELD OF THE INVENTION

The present invention relates to new 2,3-dihydro-isoindol-1-one derivatives, to processes for their preparation, and to pharmaceutical compositions containing them. These compounds are selective monoamine oxidase inhibitors and, therefore, are useful for treating or preventing diseases mediated by monoamine oxidase B.

BACKGROUND OF THE INVENTION

Monoamine oxidase (MAO, EC 1.4.3.4) is a flavin-containing enzyme responsible for the oxidative deamination of endogenous monoamine neurotransmitters such as dopamine, serotonin, adrenaline, or noradrenaline, and trace amines, e.g. phenylethylamine, as well as a number of amine xenobiotics. The enzyme exists in two forms, MAO-A and MAO-B, encoded by different genes (Bach et al., Proc. Natl. Acad. Sci. USA 85:4934–4938 (1988) and differing in tissue distribution, structure and substrate specificity. MAO-A has higher affinity for serotonin, octopamine, adrenaline, and noradrenaline; whereas the natural substrates for MAO-B are phenylethylamine and tyramine. Dopamine is thought to be oxidised by both isoforms. MAO-B is widely distributed in several organs including brain (Cesura and Pletscher, Prog. Drug Research 38:171–297 (1992). Brain MAO-B activity appears to increase with age. This increase has been attributed to the gliosis associated with aging (Fowler et al., J. Neural. Transm. 49:1–20 (1980). Additionally, MAO-B activity is significantly higher in the brains of patients with Alzheimer's disease (Dostert et al., Biochem. Pharmacol. 38:55–561 (1989) and it has been found to be highly expressed in astrocytes around senile plaques (Saura et al., Neuroscience 70:755–774 (1994). In this context, since oxidative deamination of primary monoamines by MAO produces $NH_3$, aldehydes and $H_2O_2$, agents with established or potential toxicity, it is suggested that there is a rationale for the use of selective MAO-B inhibitors for the treatment of dementia and Parkinson's disease. Inhibition of MAO-B causes a reduction in the enzymatic inactivation of dopamine and thus prolongation of the availability of the neurotransmitter in dopaminergic neurons. The degeneration processes associated with age and Alzheimer's and Parkinson's diseases may also be attributed to oxidative stress due to increased MAO activity and consequent increased formation of $H_2O_2$ by MAO-B. Therefore, MAO-B inhibitors may act by both reducing the formation of oxygen radicals and elevating the levels of monoamines in the brain.

Given the implication of MAO-B in the neurological disorders mentioned above, there is considerable interest to obtain potent and selective inhibitors that would permit control over this enzymatic activity. The pharmacology of some known MAO-B inhibitors is for example discussed by Bentué-Ferrer et al. in CNS Drugs 6:217–236 (1996). Whereas a major limitation of irreversible and non-selective MAO inhibitor activity is the need to observe dietary precautions due to the risk of inducing a hypertensive crisis when dietary tyramine is ingested, as well as the potential for interactions with other medications (Gardner et al., J. Clin. Psychiatry 57:99–104 (1996), these adverse events are of less concern with reversible and selective MAO inhibitors, in particular of MAO-B. Thus, there is a need for MAO-B inhibitors with a high selectivity and without the adverse side-effects typical of irreversible MAO inhibitors with low selectivity for the enzyme.

SUMMARY OF THE INVENTION

The present invention relates to novel 2,3-dihydro-isoindol-1-one derivatives. More particularly, it is an object of the present invention to provide a compound of formula I or II

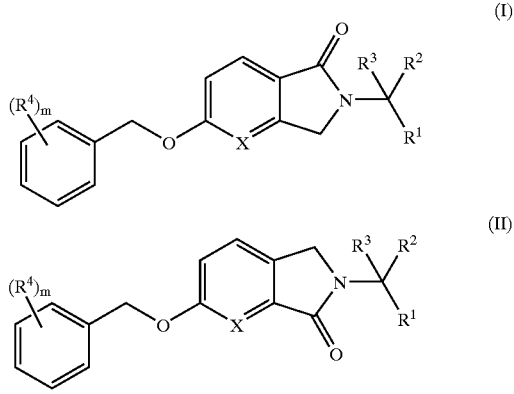

wherein X, $R^1$, $R^2$, $R^3$, $R^4$, $R^5$, $R^6$; $R^7$, $R^8$, m, n, and p are as defined herein or a pharmaceutically acceptable salt thereof. It is also an object of the invention to provide a process for the manufacture of compounds of the invention.

It has been found that the compounds of the present invention are highly selective MAO-B inhibitors. Therefore, it is another object of the present invention to provide compositions containing one or more compounds of the invention and a pharmaceutically acceptable carrier. It is a further object of the present invention to provide methods of using the compounds of the invention in the control or prevention of diseases mediated by monoamine oxidase B inhibitors, such as Alzheimer's disease, Parkinson's disease, and senile dementia.

DETAILED DESCRIPTION OF THE INVENTION

The following definitions of general terms used in the present patent application apply irrespective of whether the terms in question appear alone or in combination. It must be noted that, as used in the specification and the appended claims, the singular forms "a", "an," and "the" include plural forms unless the context clearly dictates otherwise.

The term "$(C_1$–$C_6)$-alkyl" ("lower alkyl") used in the present application denotes straight-chain or branched saturated hydrocarbon residues with 1 to 6 carbon atoms, preferably with 1 to 4 carbon atoms, such as methyl, ethyl, n-propyl, i-propyl, n-butyl, sec-butyl, t-butyl, and the like.

"$(C_1$–$C_6)$-Alkoxy" means the residue —O—R, wherein R is a lower alkyl residue as defined herein. Examples of alkoxy radicals include, but are not limited to, methoxy, ethoxy, isopropoxy, and the like.

The term "halogen" denotes fluorine, chlorine, bromine and iodine.

"Halogen-$(C_1$–$C_6)$-alkyl" or "halogen-$(C_1$–$C_6)$-alkoxy" means the lower alkyl residue or lower alkoxy residue, respectively, as defined herein substituted in any position with one or more halogen atoms as defined herein. Examples of halogenalkyl residues include, but are not limited to, 1,2-difluoropropyl, 1,2-dichloropropyl, trifluoromethyl, 2,2,2-trifluoroethyl, 2,2,2-trichloroethyl, and 1,1,1-trifluoropropyl, and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid or base.

Such salts include:

(i) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluene-sulfonic acid, trimethylacetic acid, 2,2,2-trifluoroacetic acid, and the like; or (ii) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) of the same acid addition salt.

"Therapeutically effective amount" means an amount that is effective to prevent, alleviate or ameliorate symptoms of disease or prolong the survival of the subject being treated.

The present invention relates to novel 2,3-dihydro-isoindol-1-one derivatives. More particularly, the present invention provides in a first aspect, a compound of formula I or II

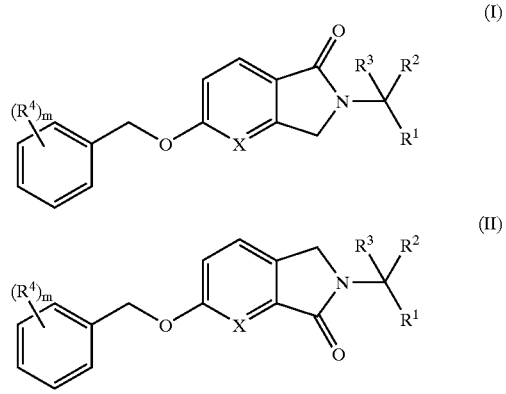

wherein

X is —N= or —CH=;

$R^1$ is —$(CH_2)_n$—CO—$NR^5R^6$, —$(CH_2)_n$—$NR^5R^6$, —$(CH_2)_n$—$COOR^7$, —$(CH_2)_n$—CN, —$(CH_2)_n$-isoindole-1,3-dionyl, or —$(CH_2)_p$—$OR^8$;

$R^2$ is hydrogen, $C_1$–$C_6$-alkyl, or OH;

$R^3$ is hydrogen or $C_1$–$C_6$-alkyl;

$R^4$ is halogen, ($C_1$–$C_6$)-alkyl, halogen-($C_1$–$C_6$)-alkyl, $C_1$–$C_6$-alkoxy or halogen-($C_1$–$C_6$)-alkoxy;

$R^5$ and $R^6$ are each independently hydrogen or $C_1$–$C_6$-alkyl;

$R^7$ is $C_1$–$C_6$-alkyl;

$R^8$ is hydrogen or $C_1$–$C_6$-alkyl;

m is 1, 2 or 3;

n is 0, 1 or 2; and p is 1 or 2;

or a pharmaceutically acceptable salt thereof.

In one embodiment the present invention provides compounds of formulae I or II wherein X is —CH=, e.g. compounds of formulae Ia or IIa

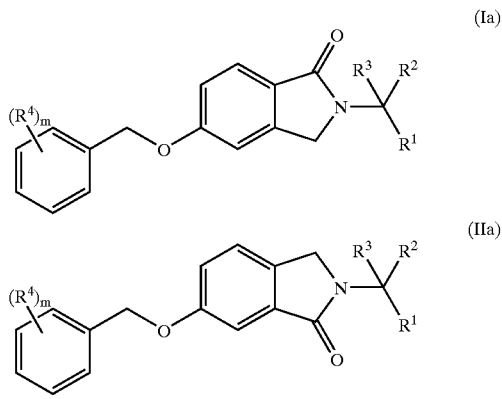

wherein $R^1$, $R^2$, $R^3$, $R^4$ and m have the above meanings.

In another embodiment the present invention provides compounds of formula I wherein $R^1$ is —$(CH_2)_n$—CO—$NR^5R^6$, —$(CH_2)_n$—$COOR^7$, —$(CH_2)_n$—CN, —$(CH_2)_n$-isoindole-1,3-dionyl, or —$(CH_2)_p$—$OR^8$, wherein $R^5$ and $R^6$ are hydrogen, $R^7$ is ($C_1$–$C_6$)-alkyl; $R^8$ is hydrogen or ($C_1$–$C_6$)-alkyl; n is 0 or 1; and p is 1. In another embodiment, the invention provides compounds of formula I wherein $R^1$ is —$(CH_2)_n$CO—$NR^5R^6$ or —$(CH_2)_p$—$OR^8$; wherein $R^5$ and $R^6$ are hydrogen; $R^8$ is ($C_1$–$C_6$)-alkyl; n is 0; and p is 1. In yet another embodiment, the invention provides compounds of formula I wherein $R^1$ is —$CONH_2$ or —$CH_2OCH_3$.

In another embodiment the present invention provides compounds of formula I wherein $R^2$ is hydrogen, ($C_1$–$C_6$)-alkyl or OH. In another embodiment, $R^2$ is hydrogen or ($C_1$–$C_6$)-alkyl. In still another embodiment, $R^2$ is hydrogen or —$CH_3$.

In another embodiment the present invention provides compounds of formula I wherein $R^3$ is hydrogen.

In another embodiment the present invention provides compounds of formula I wherein m is 1 or 2, or m is 1.

The compounds of formula I or formula II are substituted by one, two or three $R^4$ selected from the group consisting of ($C_1$–$C_6$)-alkyl, halogen, halogen-($C_1$–$C_6$)-alkyl, ($C_1$–$C_6$)-alkoxy or halogen-($C_1$–$C_6$)-alkoxy, preferably they are substituted by one $R^4$. Where the compounds are substituted by two or three $R^4$, each $R^4$ can be the same or different.

Especially preferred compounds of formula I or formula II are those, wherein $R^4$ is halogen or halogen-($C_1$–$C_6$)-alkyl. Especially preferred are those compounds of formula I, wherein $R^4$ is fluoro or trifluoromethyl.

In another embodiment the present invention provides compounds of formula I wherein X is —CH=; $R^1$ is —$(CH_2)_n$—CO—$NR^5R^6$, —$(CH_2)_n$—$COOR^7$, —$(CH_2)_n$—CN, —$(CH_2)_n$-isoindole-1,3-dionyl, or —$(CH_2)_p$—$OR^8$; $R^2$ is hydrogen, (C$_1$–C$_6$)-alkyl or OH; R$^3$ is hydrogen; R$^4$ is halogen or halogen-(C$_1$–C$_6$)-alkyl; R$^5$ and R$^6$ are hydrogen; R$^7$ is (C$_1$–C$_6$)-alkyl; R$^8$ is hydrogen or (C$_1$–C$_6$)-alkyl; m is 1 or 2; n is 0 or 1; and p is 1.

In a further embodiment the present invention provides compounds of formula I wherein X is —CH=; R$^1$ is —(CH$_2$)$_n$—CO—NR$^5$R$^6$ or —(CH$_2$)$_p$—OR$^8$; R$^2$ is hydrogen or (C$_1$–C$_6$)-alkyl; R$^3$ is hydrogen; R$^4$ is halogen or halogen-(C$_1$–C$_6$)-alkyl; R$^5$ and R$^6$ are hydrogen; R$^7$ is (C$_1$–C$_6$)-alkyl; R$^8$ is (C$_1$–C$_6$)-alkyl; m is 1; n is 0; and p is 1.

In still another embodiment the present invention provides compounds of formula I wherein X is —CH=; R$^1$ is —CONH$_2$ or —CH$_2$OCH$_3$; R$^2$ is hydrogen or —CH$_3$; R$^3$ is hydrogen; R$^4$ is F or —CF$_3$; and m is 1.

Preferred compounds of formula I are those, wherein R$^1$ is —(CH$_2$)—CO—NR$^5$R$^6$, and wherein R$^5$ and R$^6$ are each independently hydrogen or (C$_1$–C$_6$)-alkyl and n is 0, 1 or 2.

The following compounds are examples thereof:
2-[5-(3-fluoro-benzyloxy)-1-oxo-1,3-dihydro-isoindol-2-yl]-acetamide,
2-[5-(3-fluoro-benzyloxy)-1-oxo-1,3-dihydro-isoindol-2-yl]-propionamide,
(S)-2-[6-(3-fluoro-benzyloxy)-1-oxo-1,3-dihydro-isoindol-2-yl]-propionamide,
(R)-2-[6-(3-fluoro-benzyloxy)-1-oxo-1,3-dihydro-isoindol-2-yl]-propionamide,
2-[5-(4-fluoro-benzyloxy)-1-oxo-1,3-dihydro-isoindol-2-yl]-acetamide, and
2-[1-oxo-5-(4-trifluoromethyl-benzyloxy)-1,3-dihydro-isoindol-2-yl]-acetamide.

Another group of preferred compounds of formula I are those, wherein R$^1$ is —(CH$_2$)$_p$—OR$^8$, and wherein R$^8$ is (C$_1$–C$_6$)-alkyl and n is 0, 1, or 2.

5-(3-Fluoro-benzyloxy)-2-(2-methoxy-ethyl)-2,3-dihydro-isoindol-1-one is an example of such a compound.

In another embodiment the present invention provides compounds of formula II wherein R$^1$ is —(CH$_2$)$_n$—CO—NR$^5$R$^6$, —(CH$_2$)$_n$—NR$^5$R$^6$, —(CH$_2$)$_n$—COOR$^7$, —(CH$_2$)$_n$—CN, or —(CH$_2$)$_p$—OR$^8$; wherein R$^5$ and R$^6$ are hydrogen; R$^7$ is (C$_1$–C$_6$)-alkyl; R$^8$ is (C$_1$–C$_6$)-alkyl; n is 0; and p is 1. In another embodiment, the invention provides compounds of formula II wherein R$^1$ is —(CH$_2$)$_n$—CO—NR$^5$R$^6$, —(CH$_2$)$_n$—NR$^5$R$^6$, —(CH$_2$)$_n$—COOR$^7$, or —(CH$_2$)$_p$—OR$^8$; wherein R$^5$ and R$^6$ are hydrogen; R$^7$ is (C$_1$–C$_6$)-alkyl; R$^8$ is (C$_1$–C$_6$)-alkyl; m is 1; n is 0; and p is 1. In yet another embodiment, the invention provides compounds of formula II wherein R$^1$ is —CONH$_2$, —CH$_2$NH$_2$, —COOCH$_3$, or —CH$_2$OCH$_3$.

In another embodiment the present invention provides compounds of formula II wherein R$^2$ is hydrogen or (C$_1$–C$_6$)-alkyl; or R$^2$ is hydrogen or —CH$_3$.

In another embodiment the present invention provides compounds of formula II wherein R$^3$ is hydrogen.

In another embodiment the present invention provides compounds of formula II wherein R$^4$ is halogen or halogen-(C$_1$–C$_6$)-alkyl; R$^4$ is F or —CF$_3$.

In another embodiment the present invention provides compounds of formula II wherein m is 1.

In another embodiment the present invention provides compounds of formula II wherein X is —CH=; R$^1$ is —(CH$_2$)$_n$—CO—NR$^5$R$^6$, —(CH$_2$)$_n$—NR$^5$R$^6$, —(CH$_2$)$_n$—COOR$^7$, —(CH$_2$)$_n$—CN, or —(CH$_2$)$_p$—OR$^8$; R$^2$ is hydrogen or (C$_1$–C$_6$)-alkyl; R$^3$ is hydrogen; R$^4$ is halogen or halogen-(C$_1$–C$_6$)-alkyl; R$^5$ and R$^6$ are hydrogen; R$^7$ is (C$_1$–C$_6$)-alkyl; R$^8$ is (C$_1$–C$_6$)-alkyl; m is 1; n is 0; and p is 1.

In a further embodiment the present invention provides compounds of formula II wherein X is —CH=; R$^1$ is —(CH$_2$)$_n$—CO—NR$^5$R$^6$, —(CH$_2$)$_n$—NR$^5$R$^6$, —(CH$_2$)$_n$—COOR$^7$, or —(CH$_2$)$_p$—OR$^8$; R$^2$ is hydrogen or (C$_1$–C$_6$)-alkyl; R$^3$ is hydrogen; R$^4$ is halogen or halogen-(C$_1$–C$_6$)-alkyl; R$^5$ and R$^6$ are hydrogen; R$^7$ is (C$_1$–C$_6$)-alkyl; R$^8$ is (C$_1$–C$_6$)-alkyl; m is 1; n is 0; and p is 1.

In still another embodiment the present invention provides compounds of formula II wherein X is —CH=; R$^1$ is —CONH$_2$, —CH$_2$NH$_2$, —COOCH$_3$, or —CH$_2$OCH$_3$; R$^2$ is hydrogen or —CH$_3$; R$^3$ is hydrogen; R$^4$ is F or —CF$_3$; and m is 1.

Especially preferred compounds of formula II are those, wherein R$^1$ is —(CH$_2$)$_n$—CO—NR$^5$R$^6$, and wherein R$^5$ and R$^6$ are each independently hydrogen or (C$_1$–C$_6$)-alkyl and n is 0, 1 or 2.

Examples of such compounds are the following:
2-[6-(3-fluoro-benzyloxy)-1-oxo-1,3-dihydro-isoindol-2-yl]-acetamide,
(R)-2-[6-(3-fluoro-benzyloxy)-1-oxo-1,3-dihydro-isoindol-2-yl]-propionamide,
(S)-2-[1-oxo-6-(4-trifluoromethyl-benzyloxy)-1,3-dihydro-isoindol-2-yl]-propionamide, and
(R)-2-[1-oxo-6-(4-trifluoromethyl-benzyloxy)-1,3-dihydro-isoindol-2-yl]-propionamide.

Furthermore, compounds of formula II, wherein R$^1$ is —(CH$_2$)$_n$—COOR$^7$, and wherein R$^7$ is (C$_1$–C$_6$)-alkyl and n is 0, 1, or 2, are also preferred.

The following compounds are examples thereof:
[6-(3-fluoro-benzyloxy)-1-oxo-1,3-dihydro-isoindol-2-yl]-acetic acid methyl ester, and
[1-oxo-6-(4-trifluoromethyl-benzyloxy)-1,3-dihydro-isoindol-2-yl]-acetic acid methyl ester.

Further preferred compounds of formula II are those, wherein R$^1$ is —(CH$_2$)$_p$—OR$^8$, and wherein R$^8$ is (C$_1$–C$_6$)-alkyl and p is 1 or 2.

2-(2-Methoxy-ethyl)-6-(3-fluoro-benzyloxy)-2,3-dihydro-isoindol-1-one, and
2-(2-methoxy-ethyl)-6-(4-trifluoromethyl-benzyloxy)-2,3-dihydro-isoindol-1-one are examples thereof.

Also preferred are compounds of formula II, wherein R$^1$ is —(CH$_2$)$_n$—NR$^5$R$^6$, and wherein R$^5$ and R$^6$ are each independently hydrogen or (C$_1$–C$_6$)-alkyl and n is 0, 1 or 2.

The following compounds are examples thereof:
2-(2-amino-ethyl)-6-(4-trifluoromethyl-benzyloxy)-2,3-dihydro-isoindol-1-one 1:1 hydrochloride, and
2-(2-amino-ethyl)-6-(4-trifluoromethyl-benzyloxy)-2,3-dihydro-isoindol-1-one 1:1 hydrochloride.

The compounds of formulae I or II and their pharmaceutically acceptable salts can be manufactured by reacting a compound of formula III or V

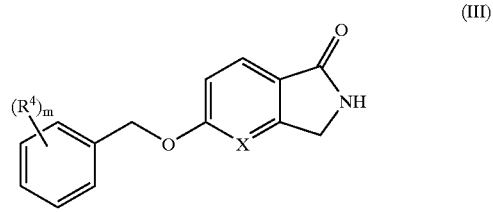

(III)

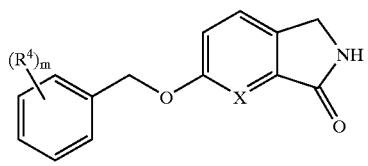

with a compound of formula IV

BrCR¹R²R³    (IV)

optionally followed by conversion into pharmaceutically acceptable salts thereof.

The compounds of formula I, Ia and Ia or II and their pharmaceutically acceptable salts can be manufactured by dissolving a compound of formula VI or VIa

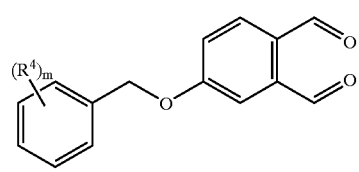

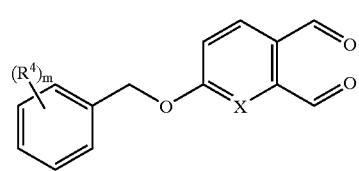

in an appropriate solvent, with or without a base, e.g. triethylamine, which is then treated with a compound of formula VII

H₂NCR¹R²R³    (VII)

optionally followed by conversion into pharmaceutically acceptable salts thereof.

The compounds of formula Ia may, e.g., be prepared following scheme 1. A compound of formula VIII may be heated in the presence of an alcohol, e.g., methanol, and an acid such as hydrochloric acid. The obtained compound IX is then halogenated, e.g., brominated by the use of, e.g., N-bromosuccinimide, to give X which in turn is transformed, e.g., in a one-pot process, to a compound of formula XI via treatment with a nucleophilic source of azide, e.g. sodium azide, reduction of the obtained compound XII with, e.g. triphenylphosphine in the presence of water, and cyclisation by heating in the presence of an alcohol, e.g. methanol. Treatment of a compound of formula XII with an O-demethylating agent, e.g. boron tribromide in dichloromethane, affords compounds of formula XIII.

Subsequently, compounds of general formula IIIa can be prepared by treating compounds of type XIII which are dissolved in a suitable solvent in the presence of a base, e.g. K₂CO₃ in DMF, in the presence of an appropriate benzyl halide. Treatment of compounds of type IIIa or III which are dissolved in THF and treated with sodium hydride and an electrophile of formula IV results in compounds of formula Ia (Scheme 2).

This scheme can correspondingly be applied to the preparation of compounds of formula I, II and IIa. All starting compounds are commercially available or may be prepared according to procedures known to the skilled artisan.

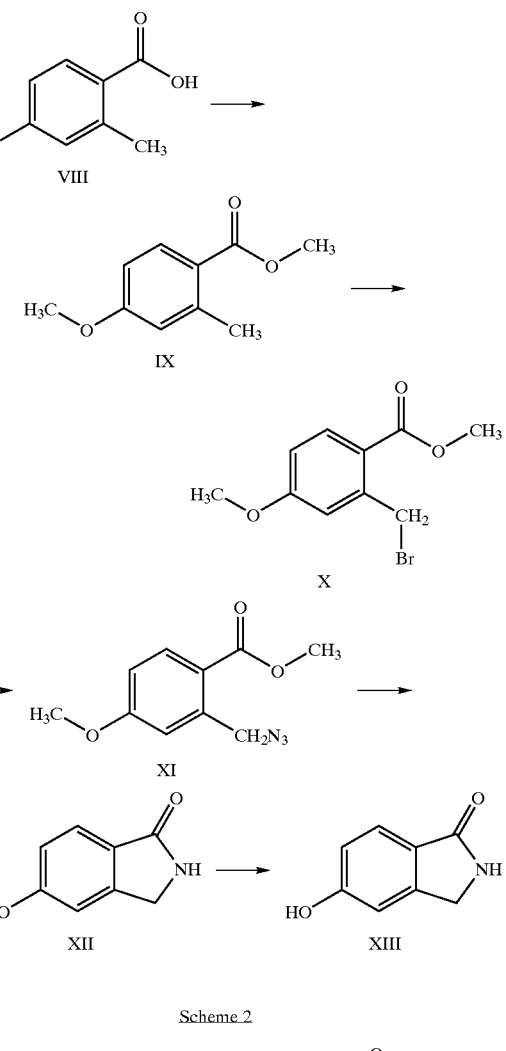

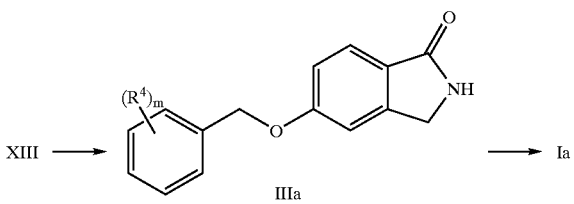

The compounds of formula Ia and IIa may, e.g., be prepared following schemes 3 and 4. Starting from the para-fluoro anisole or the 4-fluoro-3-methylanisole the acid XIV can be formed by ortho-metallation and quenching with carbon monoxide or by oxidation with KMnO₄ respectively. The product can then be transformed into the acid chloride and treated with the amine XV in dichloromethane with sodium carbonate as base. The resulting amide XVI can then be cyclised to XVII using potassium bis(trimethylsilyl)amide (KHMDS) or by treatment with 2,2,6,6-tetramethylpiperidine and n-Butyl lithium (BuLi) in THF as solvent. Treatment of XVII with aqueous sodium hydroxide affords the compound XVIII which can then be transformed into the amide XIX by treatment with a mixture of ammonium cerium nitrate (CAN) in acetonitrile water or by treatment with trifluoroacetic acid (TFA) in dichloromethane. Further reaction at low temperature with BBr₃ in dichloromethane affords the compound XX which can be elaborated to the desired products II as described above.

Scheme 3

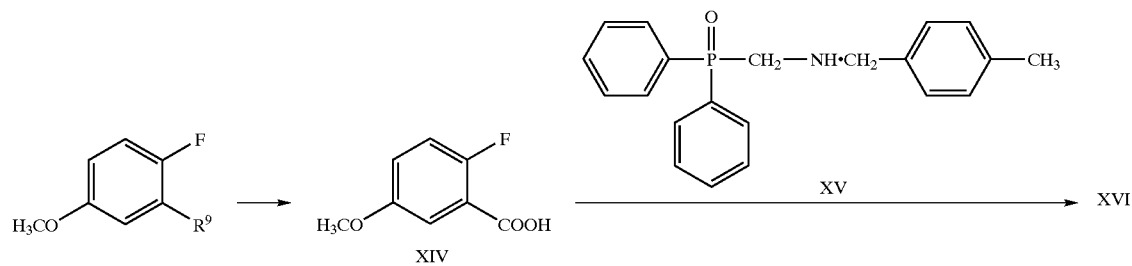

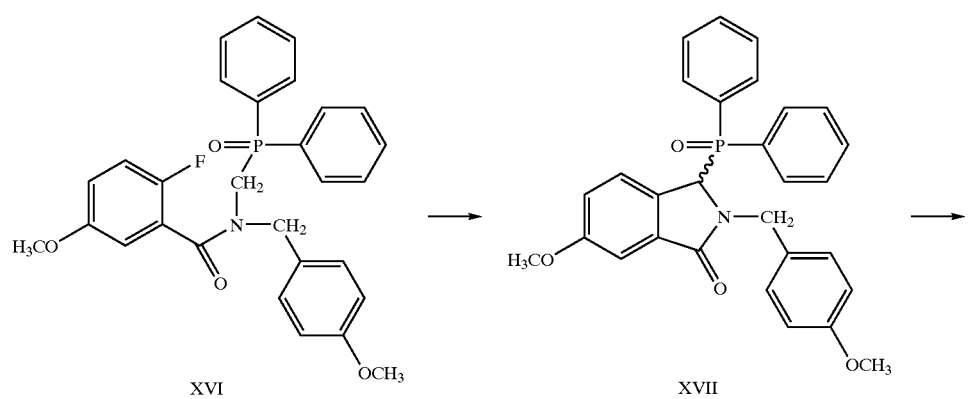

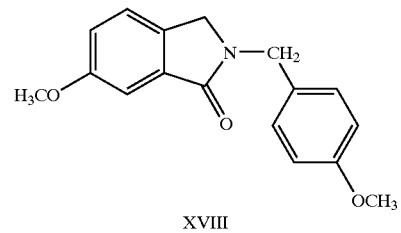

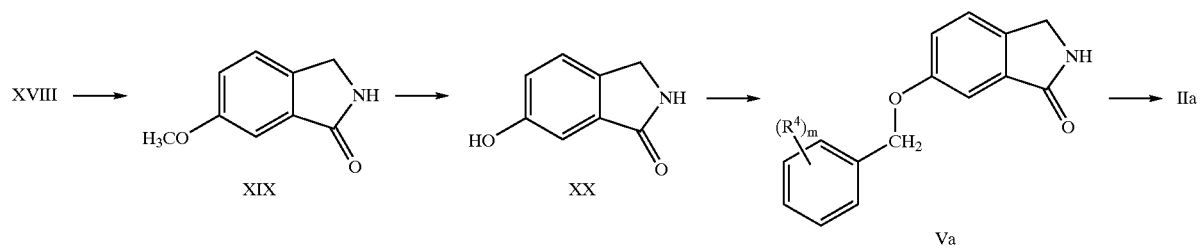

Alternatively, starting from 4-hydroxyphthalic acid XXI treatment with excess of XXII in the presence of a base such as potassium carbonate in a solution of water:THF gives the product XXIII which can be isolated and then reduced with LiAlH$_4$ in diethyl ether to afford XXIV. Oxidation using Swern conditions in dichloromethane provides access to the dialdehyde VI which can be treated with the amines VII to afford the desired products IIa or Ia by addition or exclusion of triethylamine.

Scheme 4

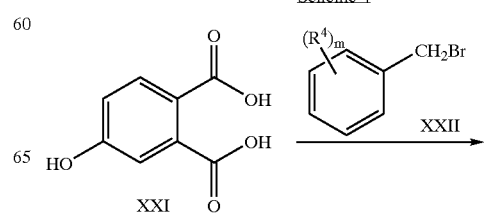

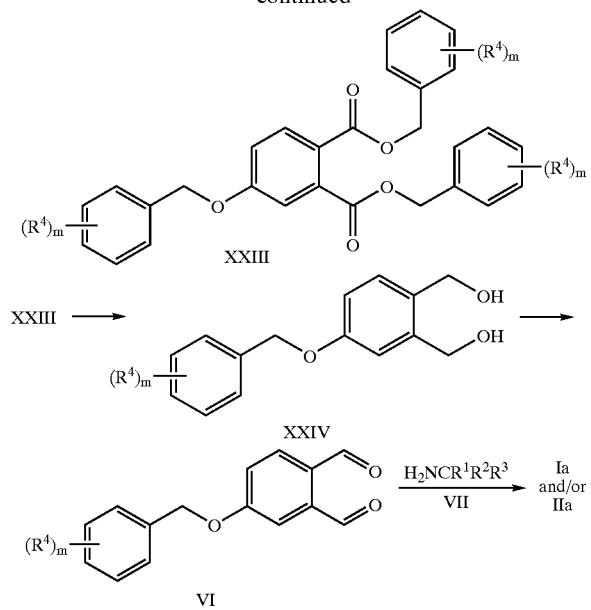

Pharmaceutically acceptable salts of compounds of formula I or II can be manufactured readily according to methods known per se and taking into consideration the nature of the compound to be converted into a salt. Inorganic or organic acids such as, for example, hydrochloric acid, hydrobromic acid) sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I or II. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I or II and their pharmaceutically acceptable salts (hereinafter: Pharmaceutical Compounds) have pharmacological activity and are useful as pharmaceuticals. In particular, Pharmaceutical Compounds exhibit monoamine oxidase B inhibitor activity and can be used for the treatment or prevention of diseases in which MAO-B inhibitors might be beneficial. These include acute and chronic neurological disorders, cognitive disorders and memory deficits. Treatable neurological disorders are for instance traumatic or chronic degenerative processes of the nervous system, such as Alzheimer's disease, other types of dementia, minimal cognitive impairment or Parkinson's disease. Other indications include psychiatric diseases such as depression, anxiety, panic attack, social phobia, schizophrenia, eating and metabolic disorders such as obesity as well as the prevention and treatment of withdrawal syndromes induced by abuse of alcohol, nicotine and other addictive drugs. Other treatable indications may be reward deficiency syndrome (WO 01/34172), peripheral neuropathy caused by cancer chemotherapy (WO 97/33572), or the treatment of multiple sclerosis (WO 96/40095) and other neuroinflammatory diseases. Pharmaceutical compounds are especially useful for the treatment and prevention of Alzheimer's disease and senile dementia.

The pharmacological activity of the compounds was tested using the following method: The cDNA's encoding human MAO-A and MAO-B were transiently transfected into EBNA cells using the procedure described by Schlaeger and Christensen [Transient Gene Expression in Mammalian Cells Grown in Serum-free Suspension Culture; Cytotechnology, 15:1–13 (1998)]. After transfection, cells were homogeneised by means of a Polytron homogeneiser in 20 mM Tris HCl buffer, pH 8.0, containing 0.5 mM EGTA and 0.5 mM phenylmethanesulfonyl fluoride. Cell membranes were obtained by centrifugation at 45,000×g and, after two rinsing steps with 20 mM Tris HCl buffer, pH 8.0, containing 0.5 mM EGTA, membranes were eventually re-suspended in the above buffer and aliquots stored at −80° C. until use.

MAO-A and MAO-B enzymatic activity was assayed in 96-well-plates using a spectro-photometric assay adapted from the method described by Zhou and Panchuk-Voloshina [A One-Step Fluorometric Method for the Continuous Measurement of Monoamine Oxidase Activity, Analytical Biochemistry 253:169–174 (1997)]. Briefly, membrane aliquots were incubated in 0.1 M potassium phosphate buffer, pH 7.4, for 30 min at 37° C. with or without various concentrations of the compounds. After this period, the enzymatic reaction was started by the addition of the MAO substrate tyramine together with 1 U/ml horse-radish peroxidase (Roche Biochemicals) and 80 $\mu$M N-acetyl-3,7,-dihydroxyphenoxazine (Amplex Red, Molecular Probes). The samples were further incubated for 30 min at 37° C. in a final volume of 200 $\mu$l and absorbance was then determined at a wavelength of 570 nm using a SpectraMax plate reader (Molecular Devices). Background (non-specific) absorbance was determined in the presence of 10 $\mu$M clorgyline for MAO-A or 10 $\mu$M L-deprenyl for MAO-B.

$IC_{50}$ values were determined from inhibition curves obtained using nine inhibitor concentrations in duplicate, by fitting data to a four parameter logistic equation using a computer program.

The compounds of the present invention are specific MAO-B inhibitors. The activities of compounds of formula I or II as measured in the assay described above are in the range of 10 $\mu$M or less, typically of 1 $\mu$M or less, and ideally 0.03 $\mu$M or less.

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions can also be in the form of suppositories or injectable solutions.

The pharmacutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They may also contain other therapeutically valuable substances.

Compounds of the present invention are selective MAO-B inhibitors. Therefore, the present invention also provides methods of treating diseases that are mediated by MAO-B. Such methods include administering a therapeutically effective amount of a compound of the invention, for example, a compound of formula I or a compound of formula II, or a pharmaceutically acceptable salt thereof, to a patient in need of such treatment. In a preferred embodiment, the invention provides a method of the treatment of Alzheimer's disease. In another preferred embodiment, the invention provides a method for the treatment of Parkinson's disease. In yet another embodiment, the present invention provides a method for the treatment of senile dementia.

The compositions of the present invention can be administered in a conventional manner, for example, orally, rectally, or parenterally. The pharmaceutical compositions of the invention can be administered orally, for example, in the form of tablets, coated tablets, dragees, hard and soft gelatine capsules, solutions, emulsions or suspensions. The pharmaceutical compositions also can be administered rectally, for example, in the form of suppositories or parenterally, for example, in the form of injection solutions.

The dosage at which the compound of the invention is administered can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The following examples are provided for illustration of the invention. They should not be considered as limiting the scope of the invention, but merely as being representative thereof. The abbreviation RT is used for "room temperature".

EXAMPLE 1

2-[5-(3-Fluoro-benzyloxy)-1-oxo-1,3-dihydro-isoindol-2-yl]-acetamide a) 4-Methoxy-2-methyl-benzoic Acid Methyl Ester According to J. Org. Chem. 33:494 (1968), a mixture of 4-methoxy-2-methylbenzoic acid (20 g, 120 mmol) and MeOH (97 mL) containing sulfuric acid (conc., 0.6 mL) was heated under reflux 48 h. After cooling the mixture was evaporated and the residue diluted with diethyl ether and washed with a saturated sodium hydrogen carbonate solution and brine. The organic phase was then separated and dried over sodium sulphate. After evaporation the residue was distilled through a 8 cm Vigreux column to afford the title compound (21.2 g, 98%) as a colourless liquid. Bp 60° C./1 mbar. MS: m/e=180.3 (M+).

b) 2-Bromomethyl-4-methoxy-benzoic Acid Methyl Ester

A mixture of 4-methoxy-2-methyl-benzoic acid methyl ester (20 g, 111 mmol), N-bromosuccinimide (20.7 g, 117 mmol) and dibenzoylperoxide (0.54 g, 2 mmol) in $CCl_4$ (150 mL) was irradiated with a 300 W lamp. The reaction maintains a steady reflux and after 4.5 h, the lamp was removed and the mixture cooled to 5° C. The mixture was then filtered, the filtrate evaporated and the residue purified twice by chromatography ($SiO_2$, Heptane:Diethyl ether: 95:5 to 85:15) to afford the title product (16.6 g, 58%) as a white solid. MS m/e=258.1 (M–H+).

c) 5-Methoxy-2,3-dihydro-isoindol-1-one

A mixture of 2-bromomethyl-4-methoxy-benzoic acid methyl ester (7.0 g, 27 mmol) and sodium azide (2.3 g, 35 mmol) in DMF (100 mL) was heated at 50° C. for 16 h. After cooling to RT the mixture was diluted with water (100 mL) and the mixture extracted with diethyl ether (3×100 mL). The combined organic phases were then washed with brine, dried over sodium sulfate. Filtration and evaporation afforded the azido product as a clear oil which was then dissolved in THF (100 mL) and then triphenylphosphine (7.1 g, 27 mmol) added followed by water (0.7 mL, 41 mmol) and the resulting mixture stirred at RT for 24 h and then heated at 55° C. for 48 h. Then MeOH (2 mL) was added and the mixture heated at 70° C. for 3 h. After cooling to RT, the mixture was evaporated and the residue purified by chromatography ($SiO_2$, $CH_2Cl_2$:2N $NH_3$-MeOH 99:1 to 94:6) to afford the title product (3.8 g, 86%) as an off-white solid. MS m/e=163.3 (M+).

d) 5-Hydroxy-2,3-dihydro-isoindol-1-one

A mixture of 5-methoxy-2,3-dihydro-isoindol-1-one (3.7 g, 23 mmol) and boron tri-bromide (1 M in $CH_2Cl_2$, 15.2 mL, 88 mmol) in $CH_2Cl_2$ (30 mL) at −78° C. was stirred for 16 h at RT. The mixture was then cooled to −78° C. and MeOH (25 mL) was added. After 1 h at −78° C. the mixture was evaporated and the residue purified by chromatography ($SiO_2$, $CH_2Cl_2$:2N $NH_3$-MeOH 98:2 to 90:10) to afford the title product (2.5 g, 72%) as an off-white solid. MS m/e=148.0 (M–H+).

e) 5-(3-Fluoro-benzyloxy)-2,3-dihydro-isoindol-1-one

A mixture of 5-hydroxy-2,3-dihydro-isoindol-1-one (2.4 g, 16 mmol), potassium carbonate (2.4 g, 18 mmol) and 3-fluorobenzyl bromide (3.3 g, 18 mmol) in acetone (40 mL) was heated under reflux for 22 h. After cooling to RT the mixture was filtered and evaporated. The residue was purified by chromatography ($SiO_2$, $CH_2Cl_2$:2N $NH_3$-MeOH 90:10) to afford the title product (2.8 g, 67%) as a white solid. MS m/e=257.2 (M+).

f) 2-[5-(3-Fluoro-benzyloxy)-1-oxo-1,3-dihydro-isoindol-2-yl]-acetamide

A mixture of 5-(3-fluoro-benzyloxy)-2,3-dihydro-isoindol-1-one (400 mg, 1.6 mmol), sodium hydride (55% in mineral oil, 75 mg, 1.7 mmol) in THF (20 mL) was stirred at RT for 45 min, and then 2-bromoacetamide (75 mg, 1.9 mmol) was added and the resulting mixture heated at 50° C. for 16 h. After cooling to RT the mixture was half-evaporated and diluted with water. The mixture was extracted with ethyl acetate and the combined organic layers were washed with brine and dried over sodium sulfate. After filtration and evaporation the residue was purified by chromatography ($SiO_2$, $CH_2Cl_2$:2N $NH_3$-MeOH 98:2 to 85:15) to afford the title product (337 mg, 67%) as a white solid. MS m/e=315.3 (M+H+).

EXAMPLE 2

2-[5-(3-Fluoro-benzyloxy)-1-oxo-1,3-dihydro-isoindol-2-yl]-propionamide

As described for example 1f, 5-(3-fluoro-benzyloxy)-2,3-dihydro-isoindol-1-one (250 mg, 0.97 mmol) was converted to the title compound (58 mg, 18%) (using 2-bromopropion-amide instead of 2-bromoacetamide) which was obtained as a white solid. MS m/e=329.3 (M+H+).

EXAMPLE 3

(S)-2-[6-(3-Fluoro-benzyloxy)-1-oxo-1,3-dihydro-isoindol-2-yl]-propionamide a) 4-(3-Fluoro-benzyloxy)-phthalic Acid Bis-(3-fluoro-benzyl)ester A mixture of 4-hydroxyphthalic acid (5.0 g, 27.5 mmol), 3-fluorobenzylbromide (31.14 g, 164.7 mmol) and potassium carbonate (15.18 g, 109.8 mmol) in THF:water (1:1, 200 mL) was heated under reflux for 72 h. After cooling to RT, the mixture was then half evaporated and the residue extracted with ethyl acetate (100 mL). The organic layer was then washed with brine, dried over sodium sulfate, filtered and evaporated. The mixture was then heated in a Kugelrohr apparatus (160° C. at 15 mmHg) to remove the excess 3-fluorobenzylbromide to leave the title compound (13.1 g, 94%) as a light yellow liquid. MS m/e=506.1 (M).

b) [5-(3-Fluoro-benzyloxy)-2-hydroxymethyl-phenyl]-methanol

To a suspension of lithium aluminum hydride (2.15 g, 56.9 mmol) and diethyl ether (150 mL) at 0° C. a solution of 4-(3-fluoro-benzyloxy)-phthalic acid bis-(3-fluoro-benzyl) ester (13.1 g, 25.9 mmol) in diethyl ether (150 mL) was added over 1 h. After a further 1.5 h water (100 mL) and sulfuric acid (2 M, 100 mL) was added and the resulting mixture was extracted with diethyl ether (2×100 mL). The combined extracts were then dried over sodium sulfate, filtered and evaporated to leave a clear oil which was purified by chromatography ($SiO_2$, hexane:ethyl acetate 1:1 to 2:3) to afford the title product (5.1 g, 76%) as a white solid. MS m/e=260.6 (M+H$^+$).

c) 4-(3-Fluoro-benzyloxy)-benzene-1,2-dicarbaldehyde

To a cooled solution of oxalyl chloride (13.3 g, 104.8 mmol) in dichloromethane (150 mL) at −78° C. a solution of DMSO (16.4 g, 209.7 mmol) in dichloromethane (35 mL) was added followed by the addition of a solution of 5-(3-fluoro-benzyloxy)-2-hydroxymethyl-phenyl]-methanol (5.1 g, 19.6 mmol) in DMSO:dichloromethane (1:3, 20 mL). Triethylamine (85.8 g, 848.3 mmol) was then added dropwise to this solution over 30 min, and the resulting reaction mixture was allowed to warm up to RT over 72 h. Then water (300 mL) was added and the product extracted with dichloromethane (2×300 mL). The combined extracts were then dried over sodium sulfate, filtered and evaporated to leave a clear oil which was purified by chromatography ($SiO_2$, hexane:ethyl acetate 3:2) to afford the title product (4.0 g, 79%) as a light brown solid. MS m/e=258.1 (M$^+$).

d) (S)-2-[6-(3-Fluoro-benzyloxy)-1-oxo-1,3-dihydro-isoindol-2-yl]-propionamide

To a cooled (0° C.) solution of 4-(3-fluoro-benzyloxy)-benzene-1,2-dicarbaldehyde (271.0 mg, 1.05 mmol) in dichlormethane (5 mL) H-Ala-NH$_2$ HCl (184.9 mg, 2.10 mmol) was added and the resulting mixture was warmed up to RT over 1 h and then heated at 50° C. for 1 h. After cooling to RT, the mixture was evaporated and the residue partioned between ethyl acetate and hydrochloric acid (1 N). The organic layer was then dried over sodium sulfate, filtered and evaporated to leave a clear oil which was purified by chromatography ($SiO_2$, dichloromethane:MeOH 9:1) to afford the title product (87 mg, 25%) as a light brown solid. MS m/e=329.2 (M+H$^+$).

EXAMPLE 4

(R)-2-[6-(3-Fluoro-benzyloxy)-1-oxo-1,3-dihydro-isoindol-2-yl]-propionamide

As described for example 3d, 4-(3-fluoro-benzyloxy)-benzene-1,2-dicarbaldehyde (250.0 mg, 0.97 mmol) was converted to the title compound (62.5 mg, 20%) (using H-D-Ala-NH$_2$ HCl instead of H-Ala-NH$_2$ HCl) which was obtained as a light brown solid. MS m/e=327.5 (M−H$^−$).

EXAMPLE 5

3-[5-(3-Fluoro-benzyloxy)-1-oxo-1,3-dihydro-isoindol-2-yl]-propionamide

As described for example 1f, 5-(3-fluoro-benzyloxy)-2,3-dihydro-isoindol-1-one (250 mg, 0.97 mmol) was converted to the title compound (166 mg, 52%) (using 3-bromopropionamide instead of 2-bromoacetamide) which was obtained as a white solid. MS m/e=329.3 (M+H$^+$).

EXAMPLE 6

[5-(3-Fluoro-benzyloxy)-1-oxo-1,3-dihydro-isoindol-2-yl]-acetic Acid Ethyl Ester As described for example 1f, 5-(3-fluoro-benzyloxy)-2,3-dihydro-isoindol-1-one (250 mg, 0.97 mmol) was converted to the title compound (242 mg, 73%) (using ethyl bromo acetate instead of 2-bromoacetamide) which was obtained as a light-yellow solid. MS=m/e 344.3 (M+H$^+$).

EXAMPLE 7

[5-(3-Fluoro-benzyloxy)-1-oxo-1,3-dihydro-isoindol-2-yl]-acetic Acid Methyl Ester As described for example 3d, 4-(3-fluoro-benzyloxy)-benzene-1,2-dicarbaldehyde (250.0 mg, 0.97 mmol) was converted to the title compound (71 mg, 22%) (using glycine methylester HCl instead of H-Ala-NH$_2$ HCl) which was obtained as a light brown solid. MS m/e=330.2 (M−H$^+$).

EXAMPLE 8

2-[5-(3-Fluoro-benzyloxy)-1-oxo-1,3-dihydro-isoindol-2-yl]-propionic Acid Ethyl Ester As described for example 1f, 5-(3-fluoro-benzyloxy)-2,3-dihydro-isoindol-1-one (250 mg, 0.97 mmol) was converted to the title compound (119 mg, 34%) (using ethyl 2-bromopropionate instead of 2-bromoacetamide) which was obtained as a light-yellow solid. MS m/e=358.3 (M+H$^+$).

EXAMPLE 9

[5-(3-Fluoro-benzyloxy)-1-oxo-1,3-dihydro-isoindol-2-yl]-acetic Acid Tert-butyl Ester As described for example 1f, 5-(3-fluoro-benzyloxy)-2,3-dihydro-isoindol-1-one (250 mg, 0.97 mmol) was converted to the title compound (187 mg, 52%) (using tert-butyl bromoacetate instead of 2-bromoacetamide) which was obtained as a light-yellow solid. MS m/e=372.3 (M+H$^+$).

EXAMPLE 10

[5-(3-Fluoro-benzyloxy)-1-oxo-1,3-dihydro-isoindol-2-yl-hydroxy-acetic Acid Ethyl Ester As described for example 1f, 5-(3-fluoro-benzyloxy)-2,3-dihydro-isoindol-1-one (250 mg, 0.97 mmol) was converted to the title compound (8 mg, 2%) (using ethyl bromofluoro-acetate instead of 2-bromoacetamide) which was obtained as a light-yellow solid. MS m/e=360.3 (M+H$^+$).

EXAMPLE 11

5-(3-Fluoro-benzyloxy)-2-(2-methoxy-ethyl)-2,3-dihydro-isoindol-1-one

As described for example 1f, 5-(3-fluoro-benzyloxy)-2,3-dihydro-isoindol-1-one (150 mg, 0.58 mmol) was converted to the title compound (33 mg, 18%) (using 2-bromoethyl methylether instead of 2-bromoacetamide) which was obtained as an off-white solid. MS m/e=315.2 (M$^+$).

EXAMPLE 12

2-{3-[5-(3-Fluoro-benzyloxy)-1-oxo-1,3-dihydro-isoindol-2-yl]-propyl}-isoindole-1,3-dione As described for example 1f, 5-(3-fluoro-benzyloxy)-2,3-dihydro-isoindol-1-one (250 mg, 0.97 mmol) was converted to the title compound (35 mg, 8%) (using N-(3-bromopropyl)-phthalimide instead of 2-bromoacetamide) which was obtained as a yellow solid. MS m/e=445.4 (M$^+$).

EXAMPLE 13

5-(3-Fluoro-benzyloxy)-2-(2-hydroxy-ethyl)-2,3-dihydro-isoindol-1-one a) 5-Methoxy-2-(2-methoxy-ethyl)-2,3-dihydro-isoindol-1-one A mixture of 2-bromomethyl-4-methoxy-benzoic acid methyl ester (1.0 g, 3.9 mmol), triethylamine (391 mg, 3.9 mmol) and 2-methoxy-ethylamine (348 mg, 4.6 mmol) was heated under reflux for 2 h. After cooling to RT the mixture was filtered and evaporated. The residue was purified by chromatography (SiO$_2$, Heptane:EtOAc 1:1 to EtOAc) to afford the title product (260 mg, 30%) as a light yellow solid. MS m/e=221.3 (M$^+$).

b) 5-Hydroxy-2-(2-hydroxy-ethyl)-2,3-dihydro-isoindol-1-one

A mixture of 5-methoxy-2-(2-methoxy-ethyl)-2,3-dihydro-isoindol-1-one (150 mg, 0.68 mmol) and boron tribromide (1 M in CH$_2$Cl$_2$, 1.4 mL, 1.36 mmol) in CH$_2$Cl$_2$ (8 mL) at −78° C. was stirred for 16 h at RT. The mixture was then cooled to −78° C. and MeOH (25 mL) was added. After 1 h at −78° C. the mixture was evaporated and the residue purified by chromatography (SiO$_2$, CH$_2$Cl$_2$:2N NH$_3$-MeOH 98:2 to 90:10) to afford the title product (42 mg, 32%) as a light orange solid. MS m/e=193.3 (M$^+$).

c) 5-(3-Fluoro-benzyloxy)-2-(2-hydroxy-ethyl)-2,3-dihydro-isoindol-1-one

As described for example 1e, 5-(3-fluoro-benzyloxy)-2-(2-hydroxy-ethyl)-2,3-dihydro-isoindol-1-one (30 mg, 0.16 mmol) was converted to the title compound (11 mg, 24%) which was obtained as a white solid. MS m/e=301.1 (M$^+$).

EXAMPLE 14

2-[5-(4-Fluoro-benzyloxy)-1-oxo-1,3-dihydro-isoindol-2-yl]-acetamide a) 5-(4-Fluoro-benzyloxy)-2,3-dihydro-isoindol-1-one As described for example 1e, 5-hydroxy-2,3-dihydro-isoindol-1-one (190 mg, 1.28 mmol) was converted to the title compound (236 mg, 72%) (using 4-fluoromethylbenzyl bromide instead of 3-fluorobenzyl bromide) which was obtained as a white solid. MS m/e=257.9 (M+H$^+$).

b) 2-[5-(4-Fluoro-benzyloxy)-1-oxo-1,3-dihydro-isoindol-2-yl]-acetamide

As described for example 1f, 5-(4-fluoro-benzyloxy)-2,3-dihydro-isoindol-1-one (200 mg, 0.65 mmol) was converted to the title compound (127 mg, 52%) which was obtained as a white solid. MS m/e=315.2 (M+H$^+$).

EXAMPLE 15

2-[1-Oxo-5-(4-trifluoromethyl-benzyloxy)-1,3-dihydro-isoindol-2-yl]-acetamide a) 5-(4-Trifluoromethyl-benzyloxy)-2,3-dihydro-isoindol-1-one As described for example 1e, 5-hydroxy-2,3-dihydro-isoindol-1-one (190 mg, 1.28 mmol) was converted to the title compound (287 mg, 73%) (using 4-trifluoromethylbenzyl bromide instead of 3-fluorobenzyl bromide) which was obtained as a white solid. MS m/e=308.1 (M+H$^+$).

b) 2-[1-Oxo-5-(4-trifluoromethyl-benzyloxy)-1,3-dihydro-isoindol-2-yl]-acetamide As described for example 1f, 5-(4-trifluoromethyl-benzyloxy)-2,3-dihydro-isoindol-1-one (200 mg, 0.78 mmol) was converted to the title compound (133 mg, 47%) which was obtained as a white solid. MS m/e=365.2 (M+H$^+$).

EXAMPLE 16

[1-Oxo-5-(4-trifluoromethyl-benzyloxy)-1,3-dihydro-isoindol-2-yl]-acetonitrile a) 4-(4-Trifluoromethyl-benzyloxy)-phthalic Acid Bis-(4-trifluoromethyl-benzyl)ester As described for example 3a, 4-hydroxyphthalic acid (5.0 g, 27.5 mmol) was converted to the title compound (12.5 mg, 69%) (using 4-(trifluoromethyl)-benzylbromide instead of 3-fluorobenzylbromide) which was obtained as a white solid. MS m/e 674.2 (M+H$_2$O+).

b) [2-Hydroxymethyl-5-(4-trifluoromethyl-benzyloxy)-phenyl]-methanol

As described for example 3b, 4-(4-trifluoromethyl-benzyloxy)-phthalic acid bis-(4-trifluoromethyl-benzyl)ester (12.5 g, 19.0 mmol) was converted to the title compound (4.8 g, 80%) which was obtained as a white solid. MS m/e=331.0 (M−H$^-$).

c) 4-(4-Trifluoromethyl-benzyloxy)-benzene-1,2-dicarbaldehyde

As described for example 3c, [2-hydroxymethyl-5-(4-trifluoromethyl-benzyloxy)phenyl]-methanol (4.75 g, 15.2 mmol) was converted to the title compound (3.95 g, 84%) which was obtained as a light yellow solid. MS m/e 308.1 (M$^+$)

d) [1-Oxo-5-(4-trifluoromethyl-benzyloxy)-1,3-dihydro-isoindol-2-yl]-acetonitrile To a cooled (0° C.) solution of 4-(4-trifluoromethyl-benzyloxy)-benzene-1,2-dicarbaldehyde (250.0 mg, 0.81 mmol) in DMF (7 mL) was added aminoacetonitrile HCl (150.1 mg, 1.62 mmol) and triethylamine (164.1 mg, 1.62 mmol) and the resulting mixture was warmed up to RT over 1 h and then heated at 50° C. for 1 h. After cooling to RT, the mixture was evaporated and the residue partioned between ethyl acetate and hydrochloric acid (1 N). The organic layer was then dried over sodium sulfate, filtered and evaporated to leave a clear oil which was purified by chromatography (SiO$_2$, DCM:MeOH 9:1) to afford the title product (19.6 mg, 7%) as a light brown solid. MS m/e 345.2 (M−H$^-$).

EXAMPLE 17

2-[5-(3,5-Bis-trifluoromethyl-benzyloxy)-1-oxo-1,3-dihydro-isoindol-2-yl]-acetamide a) 5-(3,5-Bis-trifluoromethyl-benzyloxy)-2,3-dihydro-isoindol-1-one As described for example 1e, 5-hydroxy-2,3-dihydro-isoindol-1-one (170 mg, 1.13 mmol) was converted to the title compound (305 mg, 71%) (using 3,5-bis(trifluoromethyl)benzyl bromide instead of 3-fluorobenzyl bromide) which was obtained as a white solid. MS m/e=376.2 (M+H$^+$).

b) 2-[5-(3,5-Bis-trifluoromethyl-benzyloxy)-1-oxo-1,3-dihydro-isoindol-2-yl]-acetamide As described for example 1f, 5-(3,5-bis-trifluoromethyl-benzyloxy)-2,3-dihydro-isoindol-1-one (200 mg, 0.53 mmol) was converted to the title compound (118 mg, 51%) which was obtained as a white solid. MS m/e=433.2 (M+H$^+$).

EXAMPLE 18

2-[6-(3-Fluoro-benzyloxy)-1-oxo-1,3-dihydro-isoindol-2-yl]-acetamide a) 2-Fluoro-5-methoxy-benzoic Acid To a vigorously stirred mixture of 4-fluoro-3-methylanisole (12.0 g, 85.6 mmol) and pyridine (41.7 g, 527 mmol) in water (170 mL) at 50° C. was added portion-wise potassium permanganate (44.65 g, mmol) and then maintained at this temperature for 2 h. The resulting mixture was then allowed to cool to RT and allowed to stand overnight and then heated for a further 5 h at 50° C. Then the mixture was filtered over celite and then the residue was washed with sulfuric acid (conc. 100 mL). The combined filtrates were then half-evaporated and neutralised with potasssium carbonate. Then the mixture was washed with diethyl ether and then the aqueous layer was acidified with hydrochloric acid (conc.) and the product extracted with diethyl ether. The combined extracts were then dried over sodium sulphate. After filtration and evaporation the crude solid was recrystallised from 1,2,-dichloroethane to afford the title compound (4.4 g, 30%) as a light pink solid. MS m/e=168.9 (M–H).

Alternatively, a solution of 4-fluoroanisole (500 mg, 4.0 mmol) in THF (10 mL) was added to a cooled solution (–78° C.) of 2,2,6,6-tetramethylpiperidine (1.1 g, 7.9 mmol) and BuLi (5 mL, 1.6 M in hexanes, 7.9 mmol) in THF (10 mL) at a slow rate to maintain the temperature below –70° C. The mixture was maintained at this temperature for 12 h, and then dry CO$_2$ gas was passed into the solution. The resulting mixture was allowed to warm up to 0° C. and then HCl (1 M, 10 mL) was added and the product was extracted with diethyl ether. The combined organic extracts were then dried over sodium sulfate, washed with water and brine, filtered and evaporated. The crude solid was then partioned between sodium hydroxide (1 M, 10 mL) and diethyl ether. The aqueous phase was then acidified with HCl (1 M) and the product extracted with diethyl ether. Evaporation afforded the title compound (268 mg, 40%) as a white solid. MS m/e=168.9 (M–H).

b) 2-Fluoro-5-methoxy-benzoyl Chloride

A mixture of 2-fluoro-5-methoxy-benzoic acid (4.3 g, 25 mmol) and thionyl chloride (68 mL, 937 mmol) and DMF (1 drop) was stirred at RT for 14 hours. The mixture was then evaporated to afford the title compound (4.77 g, 100%) after repeated azeotroping with toluene.

c) 1,3,5-Tris-(4-methoxy-benzyl)-[1,3,5]triazinane

Formaldehyde (8.2 g, 37% in water, 272 mmol) was added to a mixture of 4-methoxy-benzylamine (14.1 g, 103 mmol) in ethanol (10 mL) at 0° C. whereupon a white precipitate formed. The reaction mixture was stirred for 30 minutes at RT and then dissolved in ethyl acetate. The organic layer was then washed with water and brine, then dried over sodium sulfate. Filtration and evaporation afforded the title compound (15.5 g, 33%) as a white solid. MS m/e=448.3 (M+H$^+$).

d) (Diphenyl-phosphinoylmethyl)-(4-methoxy-benzyl)-amine

To a mixture of 1,3,5-tris-(4-methoxy-benzyl)-[1,3,5]triazinane (8.85 g, 19.8 mmol) in toluene (50 mL) was added diphenylphosphinoxide (4 g, 19.8 mmol) and the resulting mixture heated under reflux for 3 h. After cooling to RT the mixture was evaporated. The residue was purified by chromatography (SiO$_2$, Hexane:Acetone 1:0) to afford the title product (5.7 g, 82%) as a light yellow solid. MS m/e=352.3 (M+H$^+$).

e) N-(Diphenyl-phosphinoylmethyl)-2-fluoro-5-methoxy-N-(4-methoxy-benzyl)-benzamide To a mixture of 2-fluoro-5-methoxy-benzoyl chloride (4.77 g, 25.0 mmol) and sodium carbonate (13.4 g, 126.7 mmol) in dichloromethane (100 mL) cooled to 0° C. a solution of (diphenyl-phosphinoylmethyl)-(4-methoxy-benzyl)-amine (8.9 g, 25.3 mmol) in dichloromethane (50 mL) was added and the resulting mixture allowed to warm up to RT overnight. Then the mixture was filtered and evaporated and the residue was purified by chromatography (SiO$_2$, Hexane:Acetone 1:1) to afford the title product (7.3 g, 57%) as a light yellow solid. MS m/e=504.3 (M+H$^+$).

f) 3-(Diphenyl-phosphinoyl)-6-methoxy-2-(4-methoxy-benzyl)-2,3-dihydro-isoindol-1-one To a cooled solution (–78° C.) of 2,2,6,6-tetramethylpiperidine (5.7 g, 40.3 mmol) in THF (60 mL) BuLi (25 mL, 1.6 M in hexanes, 40.3 mmol) was added. To the resulting mixture a solution of N-(diphenyl-phosphinoylmethyl)-2-fluoro-5-methoxy-N-(4-methoxy-benzyl)-benzamide (9.2 g, 18.3 mmol) in THF (55 mL) was added at such a rate to maintain the temperature below –70° C. and maintained at this temperature for 30 min. The reaction mixture was then allowed to warm up to RT over 5 h, and diluted with ammonium chloride (200 mL). The product was then extracted with diethyl ether and the combined extracts washed with brine. The residue was then evaporated and purified by chromatography (SiO$_2$, Hexane:Acetone 1:1) to afford the title product (3.6 g, 41%) as a light yellow solid. MS m/e=484.3 (M+H$^+$).

g) 6-Methoxy-2-(4-methoxy-benzyl)-2,3-dihydro-isoindol-1-one

A mixture of 3-(diphenyl-phosphinoyl)-6-methoxy-2-(4-methoxy-benzyl)-2,3-dihydro-isoindol-1-one (1.49 g, 3.1 mmol) in THF (40 mL) containing a solution of sodium hydroxide (2.5 M, 12.4 mL, 30.8 mmol) was heated under reflux for 14 h. The solution was then cooled to RT and water (40 mL) added. The mixture was extracted with diethyl ether and the combined organic extracts washed with water and brine. The organic layer was then dried over sodium sulphate, filtered and evaporated. The residue was then purified by chromatography (SiO$_2$, Hexane:Acetone 6:4) to afford the title product (661 mg, 76%) as a light yellow solid. MS m/e=283.2 (M).

h) 6-Methoxy-2,3-dihydro-isoindol-1-one

A mixture of 6-methoxy-2-(4-methoxy-benzyl)-2,3-dihydro-isoindol-1-one (300 mg, 1.1 mmol) and ammonium ceric nitrate (2.2 g, 4.0 mmol) in acetonitrile:water (12 mL, 2:1) was stirred at RT for 1 h. Then the mixture was poured into water and extracted with ethyl acetate. The combined extracts were then washed with sodium hydrogen carbonate and water. The organic layer was then dried over sodium sulphate, filtered and evaporated. The residue was then purified by chromatography (SiO$_2$, dichloromethane:MeOH 20:1) to afford the title product (75 mg, 43%) as a light yellow solid. MS m/e=164.2 (M).

Alternatively, a mixture of 6-methoxy-2-(4-methoxybenzyl)-2,3-dihydro-isoindol-1-one (98.5 mg, 0.35 mmol) in dichlormethane (10 mL) containing TFA (1.6 mL, 20.8 mmol) and TfOH (0.6 mL, 7.0 mmol) was heated overnight at 40° C. Then the mixture was poured into sodium hydrogen carbonate and water and the product extracted with dichloromethane. The combined organic layers were then dried over sodium sulphate, filtered and evaporated. The residue was then purified by chromatography (SiO$_2$, dichloromethane:MeOH 20:1) to afford the title product (24 mg, 42%) as a light yellow solid. MS m/e=164.2 (M).

i) 6-Hydroxy-2,3-dihydro-isoindol-1-one

A mixture of 6-methoxy-2,3-dihydro-isoindol-1-one (167 mg, 1.0 mmol) and boron tribromide (1 M in CH$_2$Cl$_2$, 3.6 mL, 3.6 mmol) in CH$_2$Cl$_2$ (8 mL) at −78° C. was stirred for 18 h at RT. The mixture was then cooled to −78° C. and MeOH (20 mL) was added. After 2 h at −78° C. the mixture was evaporated and the residue purified by chromatography (SiO$_2$, CH$_2$Cl$_2$:2N NH$_3$-MeOH 9:1) to afford the title product (147 mg, 100%) as a white solid. MS m/e=148.0 (M−H$^+$).

j) 6-(3-Fluoro-benzyloxy)-2,3-dihydro-isoindol-1-one

A mixture of 6-hydroxy-2,3-dihydro-isoindol-1-one (125.0 mg, 0.84 mmol) and 3-fluorobenzylbromide (174.3 mg, 0.92 mmol) in acetone (5 mL) containing potassium carbonate (276.4 mg, 2.0 mmol) was heated under reflux for 17 h. After cooling to RT the mixture was filtered and evaporated. The residue was purified by chromatography (SiO$_2$, CH$_2$Cl$_2$:2N NH$_3$-MeOH 90:10) to afford the title product (180 mg, 83%) as a white solid. MS m/e=258.2 (M+H$^+$).

k) 2-[6-(3-Fluoro-benzyloxy)-1-oxo-1,3-dihydro-isoindol-2-yl]-acetamide

As described for example 1f, 6-(3-fluoro-benzyloxy)-2,3-dihydro-isoindol-1-one (100 mg, 0.39 mmol) was converted to the title compound (110 mg, 90%) which was obtained as a white solid. MS m/e=315.3 (M+H$^+$).

EXAMPLE 19

(S)-2-[6-(3-Fluoro-benzyloxy)-1-oxo-1,3-dihydro-isoindol-2-yl]-propionamide

As described for example 16d, 4-(3-fluoro-benzyloxy)-benzene-1,2-dicarbaldehyde (250.0 mg, 0.97 mmol) was converted to the title compound (90.9 mg, 24%) (using H-Ala-NH$_2$ HCl instead of aminoacetonitrile HCl) which was obtained as a light yellow solid. MS m/e=329.2 (M+H$^+$).

EXAMPLE 20

(R)-2-[6-(3-Fluoro-benzyloxy)-1-oxo-1,3-dihydro-isoindol-2-yl]-propionamide

As described for example 16d, 4-(3-fluoro-benzyloxy)-benzene-1,2-dicarbaldehyde (250.0 mg, 0.97 mmol) was converted to the title compound (61.9 mg, 20%) (using H-D-Ala-NH$_2$ HCl instead of aminoacetonitrile HCl) which was obtained as a light yellow solid. MS m/e=329.3 (M+H$^+$).

EXAMPLE 21

[6-(3-Fluoro-benzyloxy)-1-oxo-1,3-dihydro-isoindol-2-yl]-acetic Acid Methyl Ester As described for example 16d, 4-(3-fluoro-benzyloxy)-benzene-1,2-dicarbaldehyde (250.0 mg, 0.97 mmol) was converted to the title compound (60.2 mg, 17%) (using glycine methylester HCl instead of aminoacetonitrile HCl) which was obtained as a light brown solid. MS m/e=330.2 (M+H$^+$).

EXAMPLE 22

2-(2-Methoxy-ethyl)-6-(3-fluoro-benzyloxy)-2,3-dihydro-isoindol-1-one

As described for example 3d, 4-(3-fluoro-benzyloxy)-benzene-1,2-dicarbaldehyde (250.0 mg, 0.97 mmol) was converted to the title compound (35.0 mg, 19%) (using 2-methoxymethylamine instead of H-Ala-NH$_2$ HCl) which was obtained as a colourless gum. MS m/e=316.3 (M+H$^+$).

EXAMPLE 23

[6-(3-Fluoro-benzyloxy)-1-oxo-1,3-dihydro-isoindol-2-yl]-acetonitrile

As described for example 3d, 4-(3-fluoro-benzyloxy)-benzene-1,2-dicarbaldehyde (250.0 mg, 0.97 mmol) was converted to the title compound (38.2 mg, 13%) (using aminoacetonitrile HCl instead of H-Ala-NH$_2$ HCl) which was obtained as a white solid. MS m/e=297.3 (M+H$^+$).

EXAMPLE 24

2-(2-Amino-ethyl)-6-(4-trifluoromethyl-benzyloxy)-2,3-dihydro-isoindol-1-one 1:1 Hydrochloride a) {2-[1-Oxo-6-(4-trifluoromethyl-benzyloxy)-1,3-dihydro-isoindol-2-yl]-ethyl}-carbamic Acid Tert-butyl Ester As described for example 3d, 4-(3-fluoro-benzyloxy)-benzene-1,2-dicarbaldehyde (250.0 mg, 0.97 mmol) was converted to the title compound (62.5 mg, 16%) (using tert-butyl N-(2-aminoethyl)-carbamate instead of H-Ala-NH$_2$ HCl) which was obtained as a white solid. MS m/e=401.4 (M+H$^+$).

b) 2-(2-Amino-ethyl)-6-(4-trifluoromethyl-benzyloxy)-2,3-dihydro-isoindol-1-one 1:1 Hydrochloride A mixture of {2-[1-oxo-6-(4-trifluoromethyl-benzyloxy)-1,3-dihydro-isoindol-2-yl]ethyl}-carbamic acid tert-butyl ester (62.5 mg, 0.16 mmol) and HCl in dioxane (4 N, 5 mL) was stirred at RT for 16 h. The precipitate was filtered off and washed with ether to afford the title compound (36.2 mg, 69%) as an off-white solid. MS m/e=301.2 (M+H$^+$).

EXAMPLE 25

(S)-2-[1-Oxo-6-(4-trifluoromethyl-benzyloxy)-1,3-dihydro-isoindol-2-yl]-propionamide As described for example 16d, 4-(4-trifluoromethyl-benzyloxy)-benzene-1,2-dicarbaldehyde (250 mg, 0.81 mmol) was converted to the title compound (55.0 mg, 18%) (using H-Ala-NH$_2$ HCl instead of aminoacetonitrile HCl) which was obtained as a light yellow solid. MS m/e=379.2 (M+H$^+$).

EXAMPLE 26

(R)-2-[1-Oxo-6-(4-trifluoromethyl-benzyloxy)-1,3-dihydro-isoindol-2-yl]-propionamide As described for example 16d, 4-(4-trifluoromethyl-benzyloxy)-benzene-1,2-dicarbaldehyde (250 mg, 0.81 mmol) was converted to the title compound (46.9 mg, 15%) (using H-D-Ala-NH$_2$ HCl instead of aminoacetonitrile HCl) which was obtained as a light yellow solid. MS m/e=379.3 (M+H$^+$).

EXAMPLE 27

[1-Oxo-6-(4-trifluoromethyl-benzyloxy)-1,3-dihydro-isoindol-2-yl]-acetic Acid Methyl Ester As described for example 16d, 4-(4-trifluoromethyl-benzyloxy)-benzene-1,2-dicarbaldehyde (250 mg, 0.81 mmol) was converted to the title compound (32.6 mg, 11%) (using H-D-Ala-NH$_2$ HCl instead of aminoacetonitrile HCl) which was obtained as a light yellow solid. MS m/e=380.2 (M+H$^+$).

EXAMPLE 28

2-(2-Methoxy-ethyl)-6-(4-trifluoromethyl-benzyloxy)-2,3-dihydro-isoindol-1-one

As described for example 3d, 4-(4-trifluoromethyl-benzyloxy)-benzene-1,2-dicarbaldehyde (250 mg, 0.81 mmol) was converted to the title compound (46.5 mg, 16%) (using 2-methoxyethylamine instead of H-Ala-NH$_2$ HCl) which was obtained as a white solid. MS m/e=366.2 (M+H$^+$).

EXAMPLE 29

-Oxo-6-(4-trifluoromethyl-benzyloxy)-1,3-dihydro-isoindol-2-yl]-acetonitrile

As described for example 3d, 4-(4-trifluoromethyl-benzyloxy)-benzene-1,2-dicarbaldehyde (250 mg, 0.81 mmol) was converted to the title compound (79.6 mg, 28%) (using aminoacetonitrile HCl instead of H-Ala-NH$_2$ HCl) which was obtained as a white solid. MS m/e=346.1 (M$^+$).

EXAMPLE 30

2-(2-Amino-ethyl)-6-(4-trifluoromethyl-benzyloxy)-2,3-dihydro-isoindol-1-one 1:1 Hydrochloride a) {2-[1-Oxo-6-(4-trifluoromethyl-benzyloxy)-1,3-dihydro-isoindol-2-yl]-ethyl}-carbamic Acid Tert-butyl Ester As described for example 24b, 4-(4-trifluoromethyl-benzyloxy)-benzene-1,2-dicarbaldehyde (250 mg, 0.81 mmol) was converted to the title compound (167.7 mg, 38%) which was obtained as a white solid. MS m/e=451.3 (M+H$^+$).

b) 2-(2-Amino-ethyl)-6-(4-trifluoromethyl-benzyloxy)-2,3-dihydro-isoindol-1-one 1:1 Hydrochloride As described for example 24b, {2-[1-oxo-6-(4-trifluoromethyl-benzyloxy)-1,3-dihydro-isoindol-2-yl]-ethyl}-carbamic acid tert-butyl ester (160.0 mg, 0.36 mmol) was converted to the title compound (93.6 mg, 68%) which was obtained as a light yellow solid. MS m/e=351.2 (M+H$^+$).

EXAMPLE A

Tablets of the following composition are produced in a conventional manner:

|  | mg/Tablet |
|---|---|
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in a conventional manner:

|  | mg/Tablet |
|---|---|
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

|  | mg/Capsule |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

EXAMPLE D

An injection solution may have the following composition and is manufactured in usual manner:

| Active substance | 1.0 mg |
|---|---|
| 1 N HCl | 20.0 µl |
| acetic acid | 0.5 mg |
| NaCl | 8.0 mg |
| phenol | 10.0 mg |
| 1 N NaOH | q.s. ad pH 5 |
| H$_2$O | q.s. ad 1 ml |

What is claimed is:

1. A compound of formula I or II

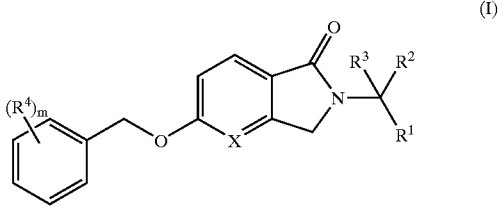

(I)

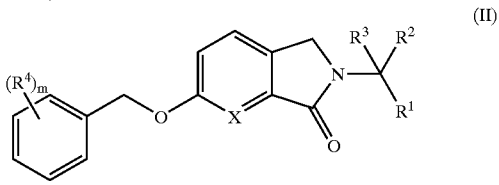

(II)

wherein

X is —N= or —CH=;

R$^1$ is —(CH$_2$)$_n$—CO—NR$^5$R$^6$, —(CH$_2$)$_n$—NR$^5$R$^6$, —(CH$_2$)$_n$—COOR$^7$, —(CH$_2$)$_n$—CN, —(CH$_2$)$_n$-isoindole-1,3-dionyl, or —(CH$_2$)$_p$—OR$^8$;

R$^2$ is hydrogen, C$_1$–C$_6$-alkyl, or OH;

$R^3$ is hydrogen or $C_1$–$C_6$-alkyl;

$R^4$ is ($C_1$–$C_6$)-alkyl, halogen, halogen-($C_1$–$C_6$)-alkyl, $C_1$–$C_6$-alkoxy or halogen-($C_1$–$C_6$)-alkoxy;

$R^5$ and $R^6$ are each independently hydrogen or $C_1$–$C_6$-alkyl;

$R^7$ is $C_1$–$C_6$-alkyl;

$R^8$ is hydrogen or $C_1$–$C_6$-alkyl;

m is 1, 2 or 3;

n is 0, 1 or 2; and p is 1 or 2;

or a pharmaceutically acceptable salt thereof.

2. A compound of claim 1 wherein m is 1 or 2.

3. A compound of claim 2 wherein m is 1.

4. A compound of claim 1 wherein $R^4$ is halogen or halogen-($C_1$–$C_6$)-alkyl.

5. A compound of claim 4 wherein $R^4$ is fluorine or trifluoromethyl.

6. A compound of claim 1 wherein X is —CH=.

7. A compound of formula I

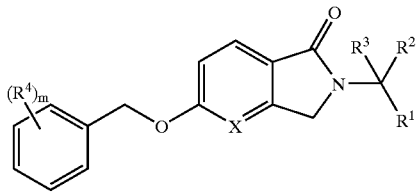

(I)

wherein

X is —N= or —CH=;

$R^1$ is —$(CH_2)_n$—CO—$NR^5R^6$, —$(CH_2)_n$—$NR^5R^6$, —$(CH_2)_n$—$COOR^7$, —$(CH_2)_n$—CN, —$(CH_2)_n$-isoindole-1,3-dionyl, or —$(CH_2)_p$—$OR^8$;

$R^2$ is hydrogen, $C_1$–$C_6$-alkyl, or OH;

$R^3$ is hydrogen or $C_1$–$C_6$-alkyl;

$R^4$ is ($C_1$–$C_6$)-alkyl, halogen, halogen-($C_1$–$C_6$)-alkyl, $C_1$–$C_6$-alkoxy or halogen-($C_1$–$C_6$)-alkoxy;

$R^5$ and $R^6$ are each independently hydrogen or $C_1$–$C_6$-alkyl;

$R^7$ is $C_1$–$C_6$-alkyl;

$R^8$ is hydrogen or $C_1$–$C_6$-alkyl;

m is 1, 2 or 3;

n is 0, 1 or 2; and p is 1 or 2;

or a pharmaceutically acceptable salt thereof.

8. A compound of claim 7 wherein $R^3$ is hydrogen.

9. A compound of claim 7 wherein m is 1 or 2.

10. A compound of claim 9 wherein m is 1.

11. A compound of claim 7 wherein $R^2$ is hydrogen or $C_1$–$C_6$-alkyl.

12. A compound of claim 11 wherein $R^2$ is hydrogen.

13. A compound of claim 11 wherein $R^2$ is methyl.

14. A compound of claim 7 wherein $R^1$ is $CONH_2$ or $CH_2OCH_3$.

15. A compound of claim 7 wherein $R^8$ is $C_1$–$C_6$-alkyl.

16. A compound of claim 15 wherein $R^1$ is —$(CH_2)_p$—$OR^8$.

17. A compound of claim 15 wherein $R^1$ is —$(CH_2)_n$—CO—$NR^5R^6$ or —$(CH_2)_p$—$OR^8$; $R^5$ and $R^6$ are hydrogen; n is 0; and p=1.

18. A compound of claim 7 wherein $R^1$ is —$(CH_2)_n$—CO—$NR^5R^6$, —$(CH_2)_n$—$COOR^7$, —$(CH_2)_n$—CN, —$(CH_2)_n$-isoindole-1,3-dionyl, or —$(CH_2)_p$—$OR^8$; $R^5$ and $R^6$ are hydrogen; n is 0 or 1; and p is 1.

19. A compound of claim 7 wherein X is —N=.

20. A compound of claim 7 wherein X is —$CH_2$—.

21. A compound of formula I

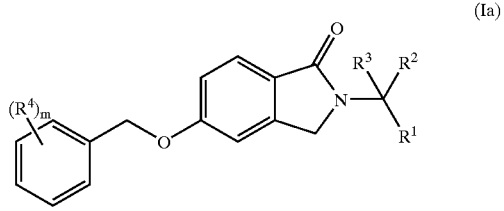

(Ia)

wherein $R^1$ is —$(CH_2)_n$—CO—$NR^5R^6$, —$(CH_2)_n$—$NR^5R^6$, —$(CH_2)_n$—$COOR^7$— $(CH_2)_n$—CN, —$(CH_2)_n$-isoindole-1,3-dionyl, or —$(CH_2)_p$—$OR^8$;

$R^2$ is hydrogen, $C_1$–$C_6$-alkyl, or OH;

$R^3$ is hydrogen or $C_1$–$C_6$-alkyl;

$R^4$ is ($C_1$–$C_6$)-alkyl, halogen, halogen-($C_1$–$C_6$)-alkyl, $C_1$–$C_6$-alkoxy or halogen-($C_1$–$C_6$)-alkoxy;

$R^5$ and $R^6$ are each independently hydrogen or $C_1$–$C_6$-alkyl;

$R^7$ is $C_1$–$C_6$-alkyl;

$R^8$ is hydrogen or $C_1$–$C_6$-alkyl;

m is 1, 2 or 3;

n is 0, 1 or 2; and p is 1 or 2;

or a pharmaceutically acceptable salt thereof.

22. A compound of claim 21 wherein $R^1$ is —$(CH_2)_n$—CO—$NR^5R^6$.

23. A compound of claim 21 wherein $R^1$ is —$(CH_2)_n$—CO—$NR^5R^6$, —$(CH_2)_n$—$COOR^7$, —$(CH_2)_n$—CN, —$(CH_2)_n$-isoindole-1,3-dionyl, or —$(CH_2)_p$—$OR^8$; $R^3$ is hydrogen; $R^4$ is halogen or halogen-($C_1$–$C_6$)-alkyl; $R^5$ and $R^6$ are hydrogen; m is 1 or 2; n is 0 or 1; and p is 1.

24. A compound of claim 21 wherein $R^1$ is —$(CH_2)_n$—CO—$NR^5R^6$ or —$(CH_2)_p$—$OR^8$; $R^2$ is hydrogen or $C_1$–$C_6$-alkyl; $R^3$ is hydrogen; $R^4$ is halogen or halogen-($C_1$–$C_6$)-alkyl; $R^5$ and $R^6$ are hydrogen; $R^8$ is $C_1$–$C_6$-alkyl; m is 1; n is 0; and p is 1.

25. A compound of claim 21 wherein $R^1$ is CO—$NH_2$ or $CH_2OCH_3$; $R^2$ is hydrogen or methyl; $R^3$ is hydrogen; $R^4$ is fluorine or trifluoromethyl; and m is 1.

26. A compound of formula II

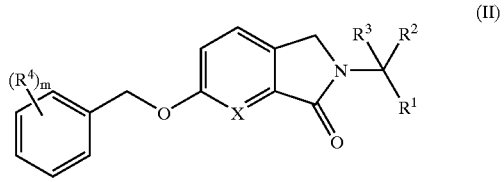

(II)

wherein

X is —N= or —CH=;

$R^1$ is —$(CH_2)_n$—CO—$NR^5R^6$, —$(CH_2)_n$—$NR^5R^6$, —$(CH_2)_n$—$COOR^7$, —$(CH_2)$—CN, —$(CH_2)_n$-isoindole-1,3-dionyl, or —$(CH_2)_p$—$OR^8$;

$R^2$ is hydrogen, $C_1$–$C_6$-alkyl, or OH;

$R^3$ is hydrogen or $C_1$–$C_6$-alkyl;

$R^4$ is ($C_1$–$C_6$)-alkyl, halogen, halogen-($C_1$–$C_6$)-alkyl, $C_1$–$C_6$-alkoxy or halogen-($C_1$–$C_6$)-alkoxy;

$R^5$ and $R^6$ are each independently hydrogen or $C_1$–$C_6$-alkyl;

$R^7$ is $C_1$–$C_6$-alkyl;

$R^8$ is hydrogen or $C_1$–$C_6$-alkyl;

m is 1, 2 or 3;

n iso, 1 or 2; and
p is 1 or 2;
or a pharmaceutically acceptable salt thereof.

27. A compound of claim 26 wherein m is 1.
28. A compound of claim 26 wherein $R^3$ is hydrogen.
29. A compound of claim 26 wherein $R^1$ is —$(CH_2)_n$—CO—$NR^5R^6$.
30. A compound of claim 26 wherein $R^1$ is —$(CH_2)_n$—$COOR^7$.
31. A compound of claim 26 wherein $R^1$ is —$(CH_2)_n$—$NR^5R^6$.
32. A compound of calim 26 wherein $R^2$ is hydrogen or $C_1$–$C_6$-alkyl.
33. A compound of claim 32 wherein $R^2$ is hydrogen.
34. A compound of claim 32 wherein $R^2$ is methyl.
35. A compound of claim 26 wherein $R^4$ is halogen or halogen-($C_1$–$C_6$)-alkyl.
36. A compound of claim 35 wherein $R^4$ is fluorine or trifluoromethyl.
37. A compound of claim 26 wherein $R^8$ is $C_1$–$C_6$-alkyl.
38. A compound of claim 37 wherein $R^1$ is —$(CH_2)_p$—$OR^8$.
39. A compound of claim 37 wherein $R^1$ is —$(CH_2)_n$—CO—$NR^5R^6$, —$(CH_2)_n$—$NR^5R^6$, —$(CH_2)_n$—$COOR^7$, —$(CH_2)_n$—CN, or —$(CH_2)_p$—$OR^8$; $R^5$ and $R^6$ are hydrogen; n is 0; and p is 1.
40. A compound of claim 37 wherein $R^1$ is —$(CH_2)_n$—CO—$NR^5R^6$, —$(CH_2)_n$—$NR^5R^6$, —$(CH_2)_n$—$COOR^7$, or —$(CH_2)_p$—$OR^8$ and m is 1.
41. A compound of claim 26 wherein $R^1$ is $CONH_2$, $CH_2NH_2$, $COOCH_3$, or $CH_2OCH_3$.
42. A compound of claim 26 wherein X=—N=.
43. A compound of formula IIa

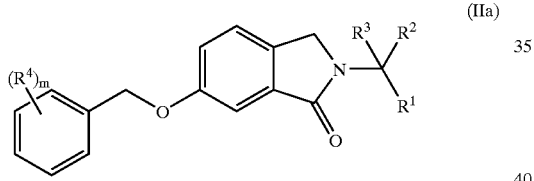

$R^1$ is —$(CH_2)_n$—CO—$NR^5R^6$, —$(CH_2)_n$—$NR^5R^6$, —$(CH_2)_n$—$COOR^7$, —$(CH_2)_n$—CN, —$(CH_2)_n$-isoindole-1,3-dionyl, or —$(CH_2)_p$—$OR^8$;
$R^2$ is hydrogen, $C_1$–$C_6$-alkyl, or OH;
$R^3$ is hydrogen or $C_1$–$C_6$-alkyl;
$R^4$ is ($C_1$–$C_6$)-alkyl, halogen, halogen-($C_1$–$C_6$)-alkyl, $C_1$–$C_6$-alkoxy or halogen-($C_1$–$C_6$)-alkoxy;
$R^5$ and $R^6$ are each independently hydrogen or $C_1$–$C_6$-alkyl;
$R^7$ is $C_1$–$C_6$-alkyl;
$R^8$ is hydrogen or $C_1$–$C_6$-alkyl;
m is 1, 2 or 3;
n is 0, 1 or 2; and
p is 1 or 2;
or a pharmaceutically acceptable salt thereof.

44. A compound of claim 43 wherein $R^1$ is —$(CH_2)_n$—CO—$NR^5R^6$, —$(CH_2)_n$—$NR^5R^6$, —$(CH_2)_n$—$COOR^7$, —$(CH_2)_n$—CN, or —$(CH_2)_p$—$OR^8$; $R^2$ is hydrogen or $C_1$–$C_6$-alkyl; $R^3$ is hydrogen; $R^4$ is halogen or halogen-($C_1$–$C_6$)-alkyl; $R^5$ and $R^6$ are hydrogen; $R^8$ is $C_1$–$C_6$-alkyl; m is 1; n is 0; and p is 1.
45. A compound of claim 43 wherein $R^1$ is —$(CH_2)_n$—CO—$NR^5R^6$, —$(CH_2)_n$—$NR^5R^6$, —$(CH_2)_n$—$COOR^7$, or —$(CH_2)_p$—OR 8; $R^2$ is hydrogen or $C_1$–$C_6$-alkyl; $R^3$ is hydrogen; $R^4$ is halogen or halogen-($C_1$–$C_6$)-alkyl; $R^5$ and $R^6$ are hydrogen; $R^8$ is $C_1$–$C_6$-alkyl; m is 1; n is 0; and p is 1.
46. A compound of claim 43 wherein $R^1$ is $CONH_2$, $CH_2NH_2$, $COOCH_3$, $CH_2OCH_3$; $R^2$ is hydrogen or methyl; $R^3$ is hydrogen; $R^4$ is fluorine or trifluoromethyl; and m is 1.
47. A composition comprising a compound of formula I or II

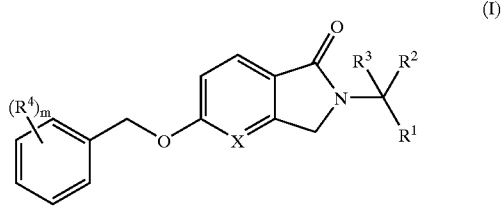

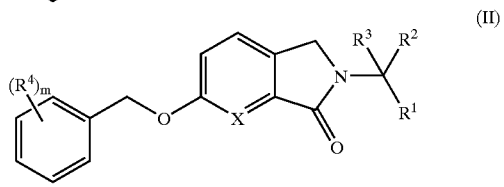

wherein
X is —N= or —CH=;
$R^1$ is —$(CH_2)_n$—CO—$NR^5R^6$, —$(CH_2)_n$—$NR^5R^6$, —$(CH_2)_n$—$COOR^7$, —$(CH_2)_n$—CN, —$(CH_2)_n$-isoindole-1,3-dionyl, or —$(CH_2)_p$—$OR^8$;
$R^2$ is hydrogen, $C_1$–$C_6$-alkyl, or OH;
$R^3$ is hydrogen or $C_1$–$C_6$-alkyl;
$R^4$ is ($C_1$–$C_6$)-alkyl, halogen, halogen-($C_1$–$C_6$)-alkyl, $C_1$–$C_6$-alkoxy or halogen-($C_1$–$C_6$)-alkoxy;
$R^5$ and $R^6$ are each independently hydrogen or $C_1$–$C_6$-alkyl;
$R^7$ is $C_1$–$C_6$-alkyl;
$R^8$ is hydrogen or $C_1$–$C_6$-alkyl;
m is 1, 2 or 3;
n is 0, 1 or 2; and
p is 1 or 2;
or a pharmaceutically acceptable salt thereof and a pharmaceutically acceptable carrier.

48. A composition of claim 47 wherein the compound is a compound of formula Ia

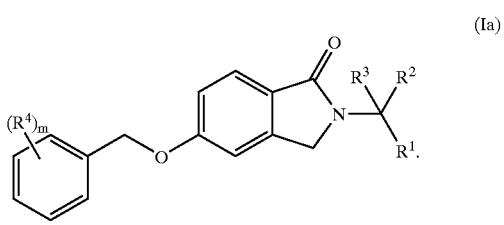

49. A composition of claim 47 wherein the compound is a compound of formula IIa

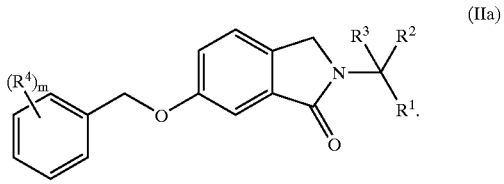

* * * * *

UNITED STATES PATENT AND TRADEMARK OFFICE
CERTIFICATE OF CORRECTION

PATENT NO. : 6,846,832 B2
DATED : January 25, 2005
INVENTOR(S) : Synese Jolidon et al.

It is certified that error appears in the above-identified patent and that said Letters Patent is hereby corrected as shown below:

Title page,
Item [73], Assignee, reads "Hoffman-La Roche Inc., Nutley, NJ (US)" should read
-- Hoffmann-La Roche Inc., Nutley, NJ (US) --.

Column 24,
Line 65, "$(CH_2)$-CN," should read -- $(CH_2)_n$-CN, --.

Column 26,
Line 57, "$(CH_2)$-CN," should read -- $(CH_2)_n$-CN, --.

Column 27,
Line 1, "n iso, 1 or 2; and" should read -- n is 0, 1 or 2; and --.
Line 64, "-$(CH_2)_p$-OR 8;" should read -- -$(CH_2)_p$-OR$^8$; --.

Signed and Sealed this

Twenty-fourth Day of May, 2005

JON W. DUDAS
*Director of the United States Patent and Trademark Office*